(12) United States Patent
Roh

(10) Patent No.: US 11,505,197 B2
(45) Date of Patent: Nov. 22, 2022

(54) METHOD AND APPARATUS FOR RELEASING SECURITY OF VEHICLE

(71) Applicant: HYUNDAI MOBIS CO., LTD., Seoul (KR)

(72) Inventor: Hee Chang Roh, Suwon-si (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 10 days.

(21) Appl. No.: 17/379,130

(22) Filed: Jul. 19, 2021

(65) Prior Publication Data

US 2022/0017098 A1    Jan. 20, 2022

(30) Foreign Application Priority Data

Jul. 20, 2020   (KR) ........................ 10-2020-0089616

(51) Int. Cl.
*G08B 13/18* (2006.01)
*B60W 40/08* (2012.01)
(Continued)

(52) U.S. Cl.
CPC ......... *B60W 40/08* (2013.01); *A61B 5/02444* (2013.01); *B60W 50/14* (2013.01); *B60W 2040/0872* (2013.01); *B60W 2050/143* (2013.01); *B60W 2420/40* (2013.01); *B60W 2420/42* (2013.01); *B60W 2420/52* (2013.01)

(58) Field of Classification Search
CPC ........ G01S 7/415; G01S 13/867; G01S 13/86; G01S 13/87; G01S 7/2813; G01S 7/4013; G01S 13/343; G01S 13/878; G01S 2013/93271; G01S 2013/93272; G01S 2013/93274; G01S 7/41; A61B 5/024; A61B 8/44; A61B 5/02444; A61B 5/0077; A61B 5/1079; A61B 5/1171; A61B 5/4887; A61B 5/7207; B60R 25/25; B60R 21/0153; B60R 25/30; B60W 2050/0052; B60W 2540/221; B60W 40/08; B60W 50/14;
(Continued)

(56) References Cited

U.S. PATENT DOCUMENTS

2018/0293401 A1* 10/2018 Weimerskirch ..... G06F 21/6245
2019/0337521 A1* 11/2019 Stauber ................ A61B 5/4803
(Continued)

*Primary Examiner* — Anh V La
(74) *Attorney, Agent, or Firm* — NSIP Law

(57) ABSTRACT

A vehicle security method includes: acquiring an input signal from a sensor unit equipped in a vehicle; setting a detection mode to a heart rate detection mode, in response to a security release operation being started, setting a radar sensor of the sensor unit to detect a target, and detecting heart rate information on the target; determining whether the heart rate information matches pre-stored heart rate information; setting the detection mode to a general detection mode, in response to the heart rate information matching the pre-stored heart rate information, measuring a distance, an azimuth, and/or an elevation angle between the vehicle and the target, and detecting body shape information of the target; determining whether the body shape information matches pre-stored body shape information; and releasing a security of a security device, in response to the body shape information matching the pre-stored body shape information.

16 Claims, 5 Drawing Sheets

(51) Int. Cl.
*A61B 5/024* (2006.01)
*B60W 50/14* (2020.01)
(58) Field of Classification Search
CPC ... B60W 2040/0872; B60W 2050/143; B60W 2420/40; B60W 2420/42; B60W 2420/52
USPC ........ 340/567, 425.5, 426.1, 426.24, 426.28, 340/426.36
See application file for complete search history.

(56) References Cited

U.S. PATENT DOCUMENTS

2020/0070657 A1\* 3/2020 Kim .......................... A61B 5/11
2020/0150758 A1\* 5/2020 Kobayashi .............. G06F 3/017

\* cited by examiner

METHOD AND APPARATUS FOR RELEASING SECURITY OF VEHICLE

CROSS-REFERENCE TO RELATED APPLICATIONS

This application claims the benefit under 35 U.S.C. § 119(a) of Korean Patent Application No. 10-2020-0089616 filed on Jul. 20, 2020 in the Korean Intellectual Property Office, the entire disclosure of which is incorporated herein by reference for all purposes.

BACKGROUND

Technical Field

The present disclosure relates to an apparatus and method for releasing security for a vehicle.

Background Art

The contents described in this section merely provide background information for the present disclosure and do not constitute the related art.

Recently, as safety and convenience functions for drivers, such as adaptive cruise control (ACC), autonomous emergency braking (AEB), and autonomous parking, have increased, the development of sensors for understanding situations around a vehicle is being actively developed. Sensors attached to the vehicle include an image sensor, LiDAR, radar, an ultrasonic sensor, or the like.

Among those, the radar sensor may accurately measure an exact distance to an object and a relative speed of an object to an observation point. Radar devices usually emit electromagnetic waves of microwaves to an object and receive the electromagnetic waves reflected from the object. The processed signals are converted into forms that may be used by operators or radar-controlled peripheral devices. Techniques of detecting motion or biometric signals using radar are being commercialized. Doppler radar uses the Doppler effect of radio waves and detects moving targets by differences between frequencies of radar waves transmitted toward the targets and frequencies of the radar waves reflected from the targets. The Doppler radar is widely used for weather radar, an autonomous navigation system of aircraft, and military radar. The Doppler radar used for meteorology measures a change in wind speed occurring inside clouds. The conventional method of measuring biometric signals using microwave radar collects, as data, the Doppler effects generated according to vibrations or movement of the human body generated by a heartbeat and breathing and measures the biometric signals.

In the process of measuring the biometric signals of the human body, additional Doppler effects are generated according to movement of the human body, movement of a muscle, or the surrounding environmental factors. Therefore, the collected signals measured by the radar include random noise in addition to the biometric signal data in the same temporal and frequency area where the biometric signals are present. Such noise lacks periodicity, and thus, has a characteristic of variously changing over time, whereas the biometric signal has a characteristic of maintaining a constant periodic pattern.

As the related art related to the present disclosure, Korean Patent Registration No. 10-1948386 discloses a method of determining a heartbeat frequency of a target by using a radar pulse reflected from the target whose heartbeat is to be measured. More specifically, Korean Patent Registration No. 10-1948386 is a technique of identifying biometric information of a target by analyzing a radar signal reflecting movement of the target.

Meanwhile, among techniques of releasing security of a vehicle, a technique of releasing facial recognition security using an image sensor has a problem in that the technique does not accurately detect a face of a driver at night or in rainy weather and therefore has low reliability, and does not accurately recognize a face upon releasing security when it is difficult to operate the image sensor.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a vehicle security method includes: in a security release start operation, acquiring an input signal from a sensor unit equipped in a vehicle and determining whether to start a security release operation; in a heart rate information detection operation, setting a detection mode to a heart rate detection mode in response to the security release operation being started, setting at least one of a frequency bandwidth, a detection angle, and a detection range of a radar sensor of the sensor unit to detect a target, and detecting heart rate information on the target; in a heart rate information determination operation, determining whether the heart rate information match pre-stored heart rate information, in response to the heart rate information being detected; in a body shape information detection operation, setting the detection mode to a general detection mode in response to the heart rate information matching the pre-stored heart rate information, measuring any one or any combination of any two or more of a distance, an azimuth, and an elevation angle between the vehicle and the target, and detecting body shape information of the target; in a body shape information determination operation, determining whether the body shape information match pre-stored body shape information; and in a security release operation, releasing a security of a security device in response to the body shape information matching the pre-stored body shape information.

The vehicle security method may further include performing a noise removing operation of filtering a signal received from the radar sensor, in the heart rate information detection operation.

The performing of the noise removing operation may include removing noise using a band-pass filter.

The performing of the noise removing operation may further include determining a frequency component outside a range of 0.66 Hz to 3 Hz as clutter and removing the frequency component.

The vehicle security method may further include not releasing the security of the security device, in response to either one of the body shape information and the heart rate information not matching the pre-stored biometric information.

The vehicle security method may further include, after the heart rate information detection operation, monitoring health information of a driver using the heart rate information.

The vehicle security method may further include notifying the driver that a health of the driver is abnormal, in response to determining, based on the monitoring of the health information of the driver, that there is an abnormality in the health information of the driver.

The vehicle security method may further include switching the radar sensor from a standby mode to a high power mode after the security release start operation.

The input signal may be generated by an image sensor included in the sensor unit.

The input signal may be generated by an infrared sensor included in the sensor unit.

In another general aspect, a non-transitory, computer-readable storage medium stores instructions that, when executed by a processor, cause the processor to perform the method described above.

In another general aspect, an apparatus with vehicle security includes: a sensor unit configured to generate an input signal and including a radar sensor configured to detect biometric information of a driver; a radar control unit configured to control the radar sensor to measure heart rate information and body shape information of the driver; and a security release control unit configured to receive the heart rate information and the body shape information from the radar control unit, and compare the heart rate information and body shape information with pre-stored biometric information to determine whether to release security of a vehicle. The security release control unit is configured to release the security of the vehicle in response to both the heart rate information and the body shape information matching the pre-stored biometric information. The security release control unit is configured to maintain the security of the vehicle in response to either one of the heart rate information and the body shape information not matching the pre-stored biometric information.

The radar control unit may be further configured to use a heart rate detection mode to measure the heart rate information, and use a general detection mode to measure the body shape information.

The radar control unit may be further configured to use band-pass filter to remove noise detected along with the heart rate information.

The band-pass filter may be configured to remove a frequency component outside a range of 0.66 Hz to 3 Hz.

The radar control unit may be further configured to notify the driver of a health abnormality of the driver, in response to a determination, based on the heart rate information, that the health abnormality has occurred.

Other features and aspects will be apparent from the following detailed description, the drawings, and the claims.

DETAILED DESCRIPTION

Figure 1:
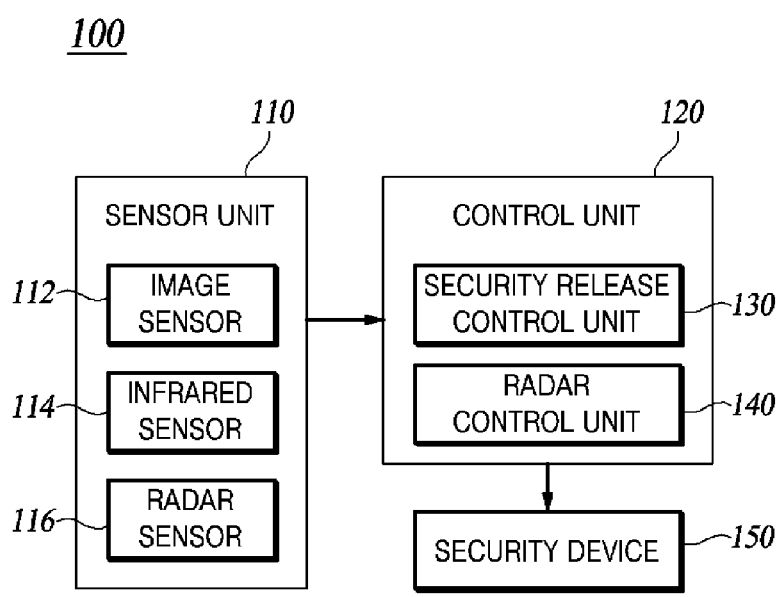
FIG. 1 is a block diagram of an apparatus for releasing security of a vehicle according to an embodiment of the present disclosure.

Some exemplary embodiments of the present disclosure are described below with reference to the accompanying drawings. In the following description, like reference numerals preferably designate like elements, although the elements are shown in different drawings. Further, in the following description of some embodiments, a detailed description of known functions and configurations incorporated herein will be omitted for the purpose of clarity and for brevity.

Additionally, alphanumeric code such as first, second, i), ii), (a), (b), etc., in numbering components are used solely for the purpose of differentiating one component from the other but not to imply or suggest the substances, the order or sequence of the components. Throughout this specification, when a part "includes" or "comprises" a component, the part is meant to further include other components, not excluding thereof unless there is an explicit description contrary thereto.

FIG. 1 is a block diagram of an apparatus for releasing security of a vehicle according to an embodiment of the present disclosure.

Referring to FIG. 1, an apparatus 100 for releasing security of a vehicle includes all or some of a sensor unit 110, a control unit 120, and a security device 150.

The sensor unit 110 includes an image sensor 112, an infrared sensor 114, and a radar sensor 116.

The plurality of sensors included in the sensor unit 110 detect biometric information, and generate an input signal for security release start control. Here, biometric information may be a heart rate, a height of a person, a body shape of a person, and the like. In the detailed description of the present disclosure, the biometric information refers to a meaning including heart rate information and body shape information. Meanwhile, the input signal may be information for a security release control unit 130 to determine whether to start security release, for example, a distance between a vehicle and a driver or the like.

A plurality of image sensors 112 may be disposed on front, rear, and left and right surfaces of a vehicle. The image sensor 112 may be disposed in a vehicle to be utilized for various functions, such as a blind spot detection function, an emergency collision prevention function, and a parking collision prevention function.

The image sensor 112 transmits image information generated by photographing views in an outward direction of the vehicle to the control unit 120. The image information may be an image, i.e., an input signal, of a driver or the like who approaches a vehicle to release security of the vehicle.

The infrared sensor 114 is a sensor that detects a difference in reflectance by using a property in which the reflectance of a lens of an eye and a cornea is different. The infrared sensor 114 includes an active type that radiates infrared rays by itself to detect a change in the radiated infrared rays, and a passive type that does not have a light emitter and detects only a change in infrared rays received from the outside. The infrared rays refer to radiation having a wavelength longer than red light of visible light and shorter than microwaves, that is, a wavelength of 0.75 μm* in an electromagnetic wave spectrum. When the infrared sensor 114 is used, sensitivity and accuracy of detecting an object are more improved compared to a conventional method of detecting an object using a temperature sensor or an ultraviolet sensor.

The infrared sensor 114 generates an input signal for the control unit 120 to start the security release control, for example, infrared information, and transmits the generated input signal to the control unit 120. For example, when the infrared sensor 114 detects that a driver who wants to release security of a vehicle approaches the vehicle, the infrared sensor 114 generates infrared information and transmits the generated infrared information to the control unit 120.

A plurality of radar sensors 116 may be disposed on the front, rear, and left and right surfaces of the vehicle. The radar sensor 116 may be disposed in a vehicle to be utilized for various functions, such as a forward vehicle tracking function, a blind spot detection function, an emergency collision prevention function, and a parking collision prevention function.

The radar sensor 116 may include a plurality of transmitting units and a plurality of receiving units. The radar signals transmitted from the transmitting units of the one or more radar sensors 116 may be received by all of the plurality of receiving units. That is, the radar sensor 116 may have a radar structure of a multi-input multi-output (MIMO) system. Each radar sensor 116 may have a field of view (FOV) of 116° to 160°.

The radar sensor 116 may be an ultra wide band (UWB) radar sensor that transmits and receives a radar signal in an ultra wide frequency band, or a frequency modulated continuous-wave (FMCW) radar sensor that transmits and receives a radar signal including a modulated frequency signal. The radar sensor 116 may adjust a detection range by adjusting an output value of a transmission signal using an amplifier (not illustrated) disposed therein.

The radar sensor 116 measures biometric information of a driver to release the security of the vehicle and transmits the measured biometric information to a radar control unit 140.

For example, the radar sensor 116 generates heart rate information of a driver when the radar control unit 140 is set to a heart rate detection mode (142a in FIG. 3) and transmits the generated heart rate information to the radar control unit 140. Meanwhile, the radar sensor 116 generates body shape information of a driver when the radar control unit 140 is set to a general detection mode (142b in FIG. 3) and transmits the generated body shape information to the radar control unit 140.

The control unit 120 includes the security release control unit 130 and the radar control unit 140.

The security release control unit 130 determines whether to start a security release operation according to the input signal measured by the sensor unit 110. For example, the input signal may be image information transmitted by the image sensor 112 or infrared information transmitted by the infrared sensor 114.

Upon receiving the image information or the infrared information, the security release control unit 130 determines that a driver has an intention to release the security of the vehicle, thereby starting the security release operation.

The radar sensor 116 waits in a standby mode when there is no attempt by a driver to release the security. On the other hand, when the security release operation is started, a mode of the radar sensor 116 is converted to a high power mode and the radar sensor 116 starts the operation.

When the security release control unit 130 starts the security release operation, the radar control unit 140 controls the radar sensor 116 to detect the heart rate information and the body shape information of a driver who wants to release the security.

When the security release operation is started, the radar control unit 140 may control to adjust a frequency bandwidth of the radar signal transmitted by the radar sensor 116, a detection angle of the radar sensor 116, or a detection range of the radar sensor 116. For example, when the security release operation is started, the radar control unit 140 may control the radar sensor 116 electronically or mechanically to change at least one of a frequency bandwidth, a detection angle, and a detection range that the radar sensor 116 detects.

The radar control unit 140 is set to the heart rate detection mode 142a or the general detection mode 142b to determine the heart rate information and/or the body shape information of the driver. The process of determining the heart rate information and the body shape information will be described in more detail with reference to FIG. 3.

The security device 150 is a locking device configured so that security of a vehicle may not be released when a person who does not match the pre-stored biometric information of the driver approaches. For example, when a driver with matching biometric information releases security, the security device 150 releases security, and when a person whose biometric information does not match attempts to release security, the security device 150 does not release security.

Figure 2:
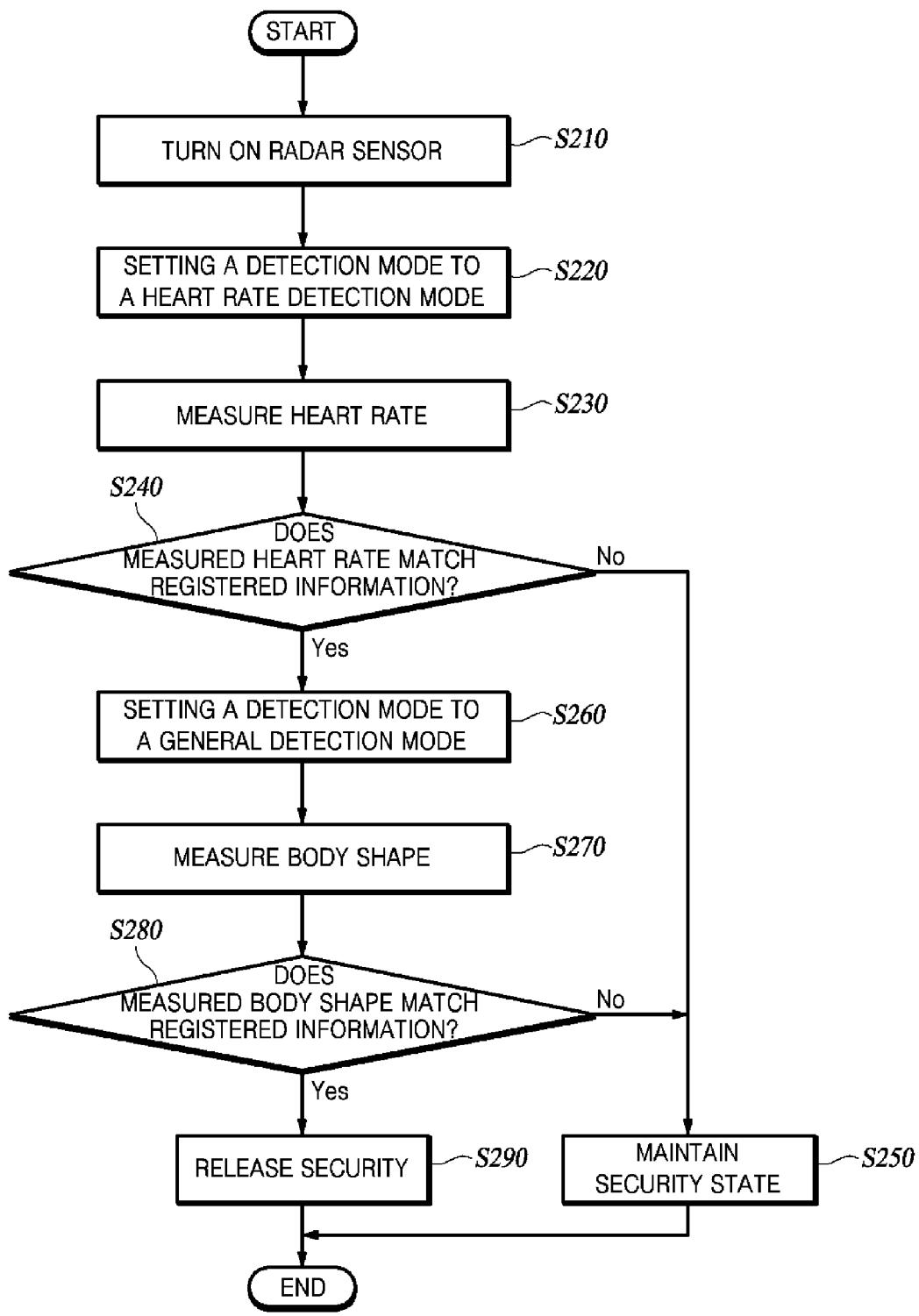
FIG. 2 is a flowchart of a method of releasing security according to an embodiment of the present disclosure.

FIG. 2 is a flowchart of a method of releasing security according to an embodiment of the present disclosure.

Referring to FIG. 2, the radar sensor 116 starts to operate for security release (S210). For example, when the security release control unit 130 receives an input signal, the radar control unit 140 may control the radar sensor 116 to start operation.

When the security release control is started and the radar sensor 116 operates, a mode of the radar control unit 140 it set to the heart rate detection mode 142a (S220), and the radar sensor 116 measures the heart rate of the driver attempting to release the security of the vehicle (S230). For example, the radar sensor 116 detects an electromagnetic wave returned by reflecting the transmitted electromagnetic wave from the driver. The heart rate information measured by the radar sensor 116 can be transmitted to the security release control unit 130.

Meanwhile, the reflected electromagnetic wave may include noise as well as the heart rate information of the driver. the radar control unit 140 may use a band-pass filter to remove signal components except for the frequency band corresponding to the radar signal transmitted by the radar sensor 116. the radar control unit 140 removes noise from the reflected electromagnetic wave using the band-pass filter.

The security release control unit 130 determines whether the received heart rate information matches the pre-stored heart rate information of the driver (S240).

When the received heart rate information and the pre-stored heart rate information of the driver do not match, the security release control unit 130 determines that a person different from a legitimate user has attempted to release security and does not release the security of the vehicle, thereby controlling to maintain the security state, for example, the locked state (S230). In this case, a driver who attempts to release security needs to use another method to release the security of the vehicle.

On the other hand, when it is determined that the received heart rate information and the pre-stored heart rate information of the driver match, the radar control unit 140 switches the measurement mode to the general detection mode 142b (S260), and the radar sensor 116 measures the body shape of the driver (S260).

the radar control unit 140 may generate the body shape information of the driver by calculating the azimuth and elevation angle of the driver with respect to the vehicle using the radar signal detected by the radar sensor 116. The generated body shape information is transmitted to the security release control unit 130.

The security release control unit 130 receives the body shape information and determines whether the received body shape information matches the pre-stored body shape information of the driver (S280). Here, the body shape information may be, for example, information on a height, a body shape, or the like.

When it is determined that the received body shape information and the pre-stored body shape information do not match, the security release control unit 130 determines that the person who attempts to release the security is not the driver, thereby controlling to maintain the security state, for example, the locked state (S250).

On the other hand, when it is determined that the received body shape information and the pre-stored body shape information match, the security release control unit 130 determines that a legitimate person is attempting to release the security of the vehicle, for example, the locking of the vehicle (S290).

Figure 3:
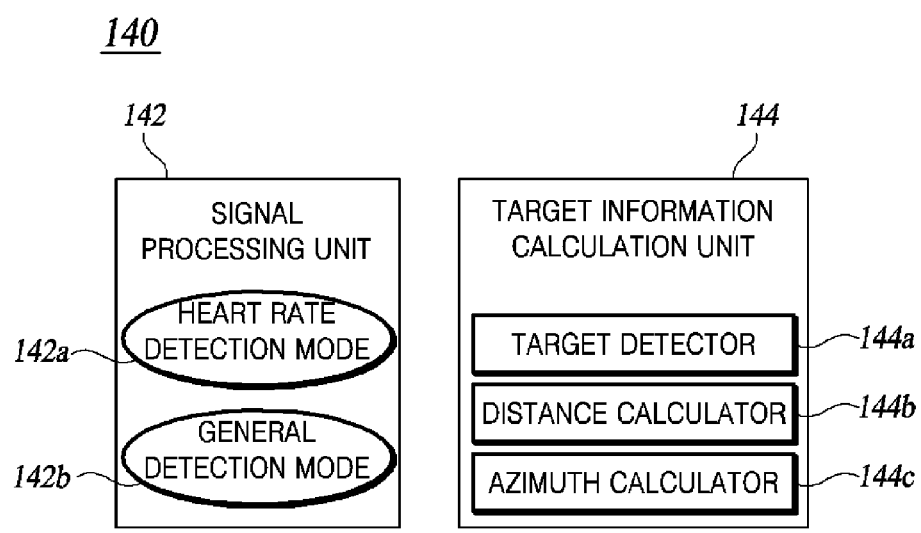
FIG. 3 is a block diagram illustrating a radar control unit according to an embodiment of the present disclosure.

FIG. 3 is a block diagram illustrating a radar control unit according to an embodiment of the present disclosure.

Referring to FIG. 3, the radar control unit 140 includes a signal processing unit 142 and a target information calculation unit 144.

When receiving a security release operation start signal from the security release control unit 130, the signal processing unit 142 sets a measurement mode to the heart rate detection mode 142a for signal processing, and when receiving a mode change signal from the security release control unit 130, the signal processing unit 142 sets the measurement mode to the general detection mode 142b for signal processing. Here, the signal processing means filtering noise mixed with valid information.

The signal processing unit 142 may change the detection mode setting according to the received signal. The signal processing unit 142 may be set to the heart rate detection mode 142a or the general detection mode 142b, and operate. The signal processing unit 142 receives the signal from the radar sensor 116 and filters signals including valid information for target detection. The number of signal processing modes is not limited to the above two.

The signal processing unit 142 basically processes the signal received from the radar sensor 116 using the heart rate detection mode 142a in the situation where the heart rate information is detected. However, the signal processing unit 142 may receive the mode change signal from the security release control unit 130 and set the detection mode to the general detection mode 142b to search for a target.

The heart rate detection mode 142a removes signal components except for a frequency band corresponding to the radar signal transmitted by the radar sensor 116 using the band-pass filter, while the heart rate detection mode 142a removes a signal received by reflecting the transmitted radar signal from, for example, a road surface. In addition to the reflected signal, a moving average method may be used to remove clutter. Here, the moving average method is a method of knowing the overall trend by using an average value of data on a time series in a certain period. Here, the clutter means unwanted noise that is reflected and received from an object that is not a radar target.

When the signal processing unit 142 is set to the heart rate detection mode 142a, the signal processing unit 142 removes signal components except for the frequency band corresponding to the heartbeat of the driver, and removes the signal received by reflecting the transmitted radar signal from the road surface. In addition, the heart rate detection mode 142a removes the clutter that is not the signal received by reflecting the transmitted radar signal by using the moving average method. In addition, when the signal processing unit 142 is set to the heart rate detection mode 142a, it is possible to increase resolution by setting the frequency bandwidth of the transmitted radar signal to a maximum value.

When the radar sensor 116 receives a radar signal reflected from the human heart, not from an obstacle made of a rigid body, the radar sensor 116 also receives information on a heartbeat frequency. Since the human heartbeat frequency is 0.66 Hertz (Hz) to 3 Hz, the heart rate detection mode 142a uses the band-pass filter to determine and remove frequency components outside a range of 0.66 Hz to 3 Hz as the clutter.

A filtering method for the signal processing unit 142 for detecting a target in the received signal to remove the clutter is not limited thereto, and those skilled in the art may add, remove, or change other types of filters. That is, the frequency range for obtaining signal information on the heartbeat of the driver may change. For example, the heart rate detection mode 142a may set the band-pass filter for removing frequency components outside a range of 0.8 Hz to 4 Hz.

The band-pass filter for detecting breathing as well as the heart rate information of the driver may be set. For example, in order to obtain the signal information on the breathing, not the heartbeat, of the driver, the signal processing unit 142 may determine frequency components outside a range of 0.1 Hz to 0.6 Hz as the clutter and remove the frequency components.

The radar control unit 140 according to the embodiment of the present disclosure may monitor the health information of the driver using the measured heart rate information. For example, when there is an abnormality in the measured heart rate information, the control unit 120 also includes a function of managing the health information of the driver, such as notifying the driver whether there is a health abnormality.

The target information calculation unit 144 may include a target detector 144a that detects a radar signal reflected from a target, a distance calculator 144b that calculates a separation distance from the detected target to the radar sensor 116, and an azimuth calculator 144c that calculates an azimuth from the radar sensor 116 to the detected target. In addition, the target information calculation unit 144 may also measure the moving speed of the target.

When the signal processed using the general detection mode 142b is received from the signal processing unit 142, the target information calculation unit 144 may detect the target. The target information calculation unit 144 measures the distance, the azimuth, or the like between the vehicle and the target. The target information calculation unit 144 calculates the information on the target and transmits the calculated information to the security release control unit 130.

In addition, when the target information calculation unit 144 receives the signal processed by the signal processing unit 142 using the heart rate detection mode 142a, the target information calculation unit 144 may detect the heartbeat of a pedestrian. Furthermore, the target information calculation unit 144 may measure a heartbeat of a pedestrian and a heart rate spectrum. The target information calculation unit 144 calculates information on heart rate detection and transmits the calculated information to the security release control unit 130.

Figure 4A:
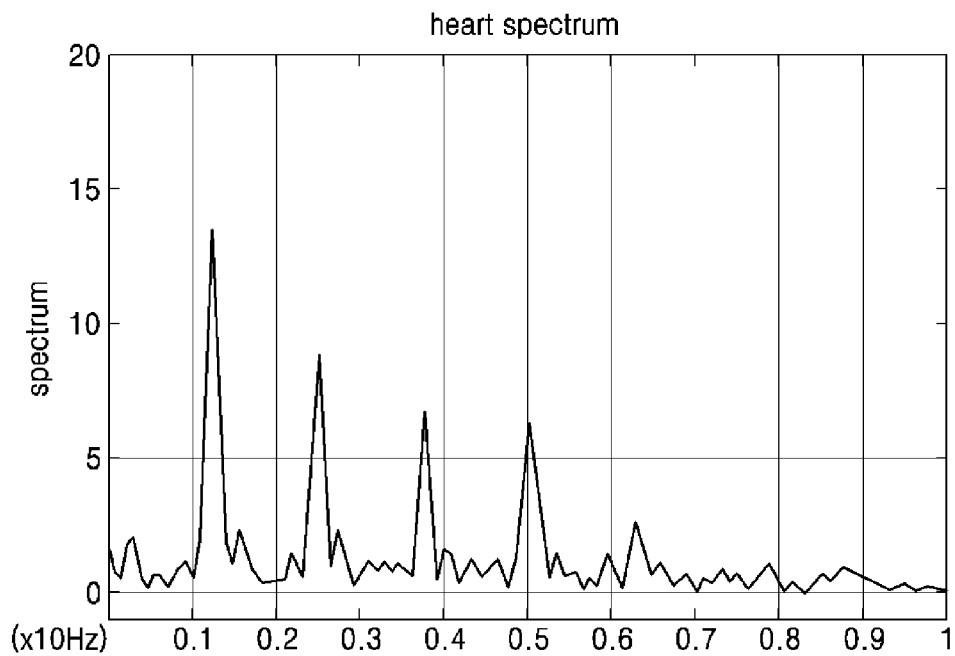
FIGS. 4A and 4B show graphs illustrating biometric signals that are a heart rate spectrum and a heart rate spectrum in which noise is mixed.
Figure 4B:
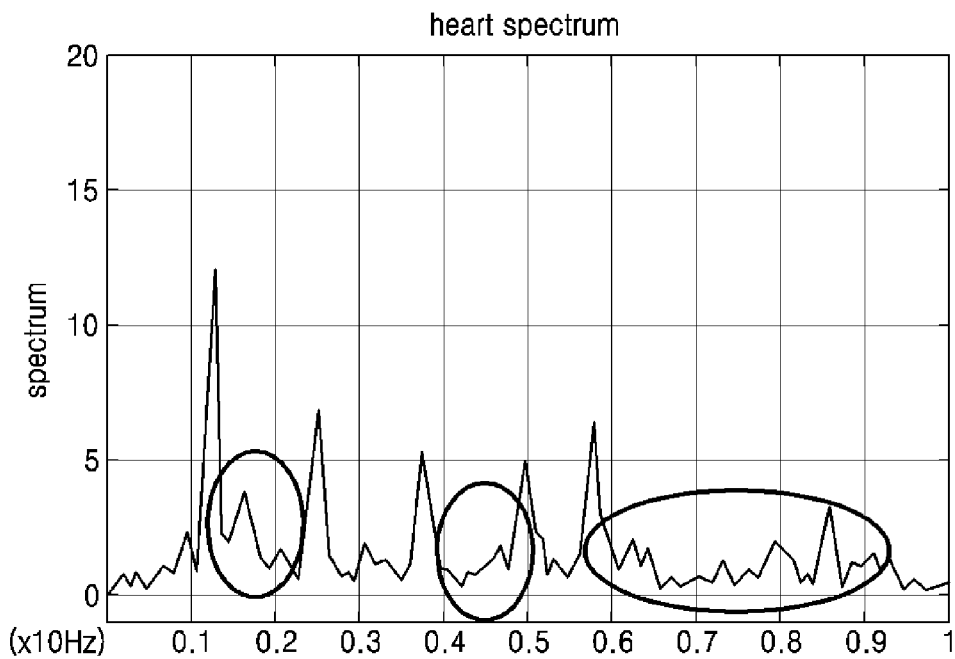

FIGS. 4A and 4B show graphs illustrating biometric signals that are a heart rate spectrum and a heart rate spectrum in which noise is mixed.

FIG. 4A is a graph illustrating a spectrum of the heart rate from which noise is removed using the band-pass filter, and FIG. 4B is a graph illustrating a heart rate spectrum and a spectrum in which noise is mixed.

Here, the noise refers to a part marked with an oval in FIG. 4B.

The security release method using biometric information detection is a method of releasing a security device 150 of a vehicle when biometric information unique to each person, for example, biometric information of a driver stored in advance using a heart rate and biometric information is recognized by a radar match.

When measuring human biometric information, additional Doppler effects occur due to movement of the human body, movement of a muscle, or surrounding environmental factors, such that noise is measured along with the biometric signal data in the collected signal detected by the radar as illustrated in FIG. 4B.

Since such noise lacks periodicity, the noise has a characteristic of appearing while variously changing over time. On the other hand, the biometric signal has a characteristic of maintaining a constant periodic pattern. Accordingly, the signal processing unit 142 according to an embodiment of the present disclosure filters the noise mixed in the human heart rate spectrum area by using the band-pass filter to distinguish the biometric signal.

Figure 5:
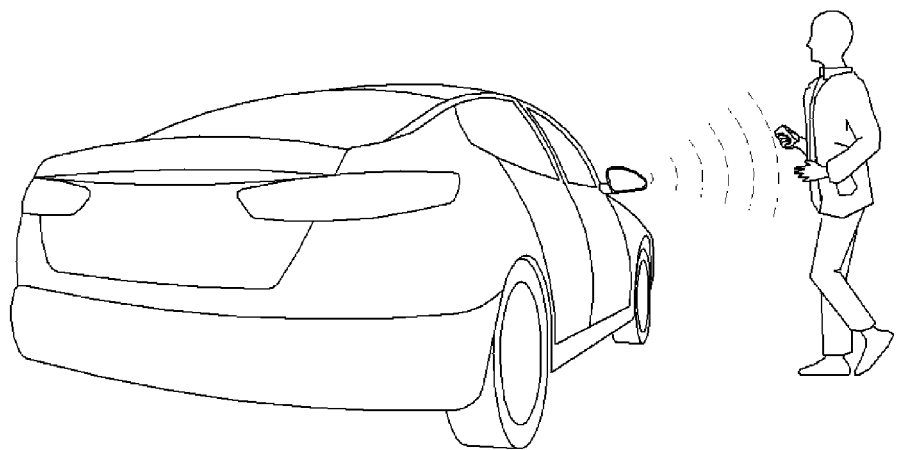
FIG. 5 is a conceptual diagram illustrating a method of emitting, by a radar sensor, a radar signal to a driver according to an embodiment of the present disclosure.

FIG. 5 is a conceptual diagram illustrating a method of emitting, by a radar sensor, a radar signal to a driver according to an embodiment of the present disclosure.

Referring to FIG. 5, when a driver approaches a vehicle, for example, a radar sensor 116 mounted on a side mirror transmits or emits electromagnetic waves to measure heart rate information and body shape information of the driver.

When the driver approaches the vehicle, the radar control unit 140 is set to the heart rate detection mode 142a to make the radar sensor to measure a heart rate of the driver.

Meanwhile, when the heart rate information matches the pre-stored heart rate information, the radar control unit 140 switches to the general detection mode 142b to make the radar sensor to measure the body shape of the driver.

Although exemplary embodiments of the present disclosure have been described for illustrative purposes, those skilled in the art will appreciate that various modifications, additions, and substitutions are possible, without departing from the idea and scope of the claimed invention. Therefore, exemplary embodiments of the present disclosure have been described for the sake of brevity and clarity. The scope of the technical idea of the present embodiments is not limited by the illustrations. Accordingly, one of ordinary skill would understand the scope of the claimed invention is not to be limited by the above explicitly described embodiments but by the claims and equivalents thereof.

REFERENCE NUMERALS

100: radar device
110: sensor unit
112: image sensor
114: infrared sensor
116: radar sensor
120: control unit
130: security release control unit
140: radar control unit
142: signal processing unit
142a: heart detection mode
142b: general detection mode
144: target information calculation unit
144a: target detector
144b: distance calculator
144c: azimuth calculator
150: security device

What is claimed is:

1. A vehicle security method, comprising:
    in a security release start operation, acquiring an input signal from a sensor unit equipped in a vehicle and determining whether to start a security release operation;
    in a heart rate information detection operation, setting a detection mode to a heart rate detection mode, in response to the security release operation being started, setting at least one of a frequency bandwidth, a detection angle, and a detection range of a radar sensor of the sensor unit to detect a target, and detecting heart rate information on the target;
    in a heart rate information determination operation, determining whether the heart rate information matches pre-stored heart rate information, in response to the heart rate information being detected;
    in a body shape information detection operation, setting the detection mode to a general detection mode, in response to the heart rate information matching the pre-stored heart rate information, measuring any one or any combination of any two or more of a distance, an azimuth, and an elevation angle between the vehicle and the target, and detecting body shape information of the target;
    in a body shape information determination operation, determining whether the body shape information matches pre-stored body shape information; and
    in a security release operation, releasing a security of a security device, in response to the body shape information matching the pre-stored body shape information.

2. The vehicle security method of claim 1, further comprising performing a noise removing operation of filtering a signal received from the radar sensor, in the heart rate information detection operation.

3. The vehicle security method of claim 2, wherein the performing of the noise removing operation comprises removing noise using a band-pass filter.

4. The vehicle security method of claim 3, wherein the performing of the noise removing operation further comprises determining a frequency component outside a range of 0.66 Hz to 3 Hz as clutter and removing the frequency component.

5. The vehicle security method of claim 1, further comprising not releasing the security of the security device, in response to either one of the body shape information and the heart rate information not matching the pre-stored biometric information.

6. The vehicle security method of claim 1, further comprising, after the heart rate information detection operation, monitoring health information of a driver using the heart rate information.

7. The vehicle security method of claim 6, further comprising notifying the driver that a health of the driver is abnormal, in response to determining, based on the monitoring of the health information of the driver, that there is an abnormality in the health information of the driver.

8. The vehicle security method of claim 1, further comprising switching the radar sensor from a standby mode to a high power mode after the security release start operation.

9. The vehicle security method of claim 1, wherein the input signal is generated by an image sensor included in the sensor unit.

10. The vehicle security method of claim 1, wherein the input signal is generated by an infrared sensor included in the sensor unit.

11. A non-transitory, computer-readable storage medium storing instructions that, when executed by a processor, cause the processor to perform the method of claim 1.

12. An apparatus with vehicle security, comprising:
- a sensor unit configured to generate an input signal and including a radar sensor configured to detect biometric information of a driver;
- a radar control unit configured to control the radar sensor to measure heart rate information and body shape information of the driver; and
- a security release control unit configured to receive the heart rate information and the body shape information from the radar control unit, and compare the heart rate information and body shape information with pre-stored biometric information to determine whether to release security of a vehicle,
- wherein, the security release control unit is configured to release the security of the vehicle in response to both the heart rate information and the body shape information matching the pre-stored biometric information, and
- wherein the security release control unit is configured to maintain the security of the vehicle in response to either one of the heart rate information and the body shape information not matching the pre-stored biometric information.

13. The apparatus of claim 12, wherein the radar control unit is further configured to use a heart rate detection mode to measure the heart rate information, and use a general detection mode to measure the body shape information.

14. The apparatus of claim 12, wherein the radar control unit is further configured to use band-pass filter to remove noise detected along with the heart rate information.

15. The apparatus of claim 14, wherein the band-pass filter is configured to remove a frequency component outside a range of 0.66 Hz to 3 Hz.

16. The apparatus of claim 12, wherein the radar control unit is further configured to notify the driver of a health abnormality of the driver, in response to a determination, based on the heart rate information, that the health abnormality has occurred.

* * * * *